(12) United States Patent
Raymond

(10) Patent No.: US 6,760,471 B1
(45) Date of Patent: Jul. 6, 2004

(54) COMPENSATION SYSTEM AND RELATED TECHNIQUES FOR USE IN A PRINTED CIRCUIT BOARD INSPECTION SYSTEM

(75) Inventor: Douglas W. Raymond, Orinda, CA (US)

(73) Assignee: Teradyne, Inc., Boston, MA (US)

( * ) Notice: Subject to any disclaimer, the term of this patent is extended or adjusted under 35 U.S.C. 154(b) by 627 days.

(21) Appl. No.: 09/602,272

(22) Filed: Jun. 23, 2000

(51) Int. Cl.[7] .................................................. G06K 9/00
(52) U.S. Cl. ........................ 382/147; 382/305; 348/126
(58) Field of Search ................................. 382/147, 281, 382/159, 293, 112, 160, 169, 172, 237, 248, 260, 276, 317, 309, 305; 345/87; 348/87, 126, 128, 247, 254, 255, 129, 297, 257, 207.99, 131, 324, 301; 250/216, 559.34, 559.07, 332, 349, 338.1, 338.4

(56) References Cited

U.S. PATENT DOCUMENTS

| | | | |
|---|---|---|---|
| 4,500,202 A | | 2/1985 | Smyth ......................... 382/100 |
| 4,801,810 A | * | 1/1989 | Koso ..................... 250/559.34 |
| 4,811,410 A | * | 3/1989 | Amir et al. ................. 382/147 |
| 5,047,861 A | * | 9/1991 | Houchin et al. ............. 348/247 |
| 5,060,065 A | * | 10/1991 | Wasserman ................ 348/247 |
| 5,245,421 A | | 9/1993 | Robertson et al. |
| 5,260,779 A | * | 11/1993 | Wasserman ................. 348/126 |
| 5,455,870 A | | 10/1995 | Sepai et al. ................. 382/147 |
| 5,519,441 A | * | 5/1996 | Gusmano et al. ........... 348/257 |
| 5,638,465 A | * | 6/1997 | Sano et al. ................. 382/281 |
| 5,757,981 A | * | 5/1998 | Kawakubo .................. 382/293 |
| 5,764,209 A | * | 6/1998 | Hawthorne et al. .......... 345/87 |
| 5,811,808 A | * | 9/1998 | Cannata et al. ............. 250/332 |
| 6,304,826 B1 | * | 10/2001 | Liu ............................ 702/104 |

FOREIGN PATENT DOCUMENTS

| | | |
|---|---|---|
| EP | 0426166 | 10/1990 |
| EP | 0 426 166 A2 | 5/1991 |

* cited by examiner

*Primary Examiner*—Bhavesh M. Mehta
*Assistant Examiner*—Sheela Chawan
(74) *Attorney, Agent, or Firm*—Daly, Crowley & Mofford; Christopher S. Daly; Teradyne Legal Dept.

(57) ABSTRACT

A system and method for compensating pixel values in an inspection machine for inspecting printed circuit boards includes an image acquisition system for providing pixel values from a digitized image to a compensation circuit. The compensation circuit applies one or more compensation values to the digitized pixel values to provide compensated digitized pixel values for storage in a memory. The compensated digitized pixel values are then available for use by an image processor which implements inspection techniques during a printed circuit board manufacturing process. With this technique, the system corrects the errors on a pixel by pixel basis as the pixel values representing an image of a printed circuit board are transferred from the image acquisition system to the memory.

10 Claims, 4 Drawing Sheets

COMPENSATION SYSTEM AND RELATED TECHNIQUES FOR USE IN A PRINTED CIRCUIT BOARD INSPECTION SYSTEM

STATEMENTS REGARDING FEDERALLY SPONSORED RESEARCH

Not Applicable.

CROSS-REFERENCE TO RELATED APPLICATIONS

Not applicable.

FIELD OF THE INVENTION

This invention relates generally to automated optical inspection (AOI) systems and more particularly to illumination systems used in AOI systems.

BACKGROUND OF THE INVENTION

As is known in the art, an automated optical inspection (AOI) system typically includes an illumination system which projects or otherwise provides light to illuminate a specimen being inspected and a camera which captures an image of the specimen and converts it to electrical signals. One or more frame grabbers transfer the electrical signals representing the image to a computer or other processing device for further processing.

It is difficult, however, to produce uniform illumination over the field of view of a camera. A processing device which is unaware of the specific nonuniformities in lighting cannot differentiate between those patterns of light in the image which are due to the appearance of the specimen and those patterns of light in the image which are due to irregularities in the illumination system.

For example, an image of a uniformly illuminated plain uniform grey surface ideally has pixel values which are all equal. In practice, however, the pixel values will not be equal unless the camera is ideal and the illumination is perfectly uniform. The computer or other processing device receives a "true" image only if the effects of nonuniform illumination can somehow be cancelled out. Nonuniformity of illumination is thus a source of noise in AOI systems.

There are a number of reasons for nonuniform illumination in AOI Systems. A typical illumination system includes one or more fluorescent lamps. On problem with fluorescent and other types of lamps is that intensity of the lamp varies along the length of the lamp. The intensity also varies with the amount of current provided to the lamp, the age of the lamp, specific variations in the manufacture of the lamp including its shape, and the temperature at which the lamp operates. It is a daunting prospect to attempt to regulate the light at one point, let alone regulate the light at all points on the object. Thus, suffice it to say that for a variety of reasons, it is relatively difficult to produce uniform illumination over the field of view of a camera.

One technique to overcome this illumination problem is to use lamps which provide relatively uniform intensity. Such lamps, however, are relatively expensive. More importantly perhaps such lamps still have variations in intensity although the variations are less severe than the intensity variations in relatively low cost lamps.

It would, therefore, be desirable to provide a system for compensating nonuniformity in an image due to variations in illumination characteristics. It would also be desirable to provide an AOI system for printed circuit boards which compensates for variations in illumination characteristics. It would be further desirable to provide a system which performs compensation in real time.

SUMMARY OF THE INVENTION

In accordance with the present invention, an automated optical inspection (AOI) system includes an image acquisition system for capturing an image and for providing a digital signal to a compensation circuit which compensates the pixel values to provide compensated or corrected pixel values. The compensation circuit provides the compensated pixel values in real time to a video frame memory and to a direct memory access (DMA) channel. The DMA channel transfers the compensated pixel values to a storage device which is coupled to or provided as part of a processor.

With this particular arrangement, an AOI system which corrects errors in a digital image due to illumination is provided. The system corrects the errors on a pixel by pixel basis as signals representing the video frame are being transferred from the image acquisition system to a frame memory. By storing compensation values in the compensation circuit and coupling the compensation circuit to a DMA channel, it is possible to compensate the pixel values in real time as the pixel values are transmitted from the image acquisition system to the frame memory. Compensating the pixels for irregularities in real time makes it possible to continue processing video information obtained by the image acquisition system at the same rate as without correction. In one embodiment, the image acquisition system includes a digital camera and in another embodiment the image acquisition system includes an analog camera having a video digitizer coupled thereto.

The details of the compensation memory architecture vary with the nature of the aberrations expected during inspection. For example, if a pure linear correction with no offset errors is expected, only a scale factor memory is needed. On the other hand, if offset errors are expected, then an offset memory is also required (e.g. to eliminate the effects of unexcludable stray light). If a nonlinear correction is needed, additional scale memories and associated arithmetic circuits to perform scale factor computations may be needed. In a preferred embodiment, only offset and scale factor are linearly corrected. It should be appreciated, however, that the concept of performing real time correction can be extended beyond simple linear calculations or reduced to simpler linear multiples without offset correction.

In preferred embodiments, the system uses a plurality of lighting modes and it may be desirable to provide the compensation memory from a plurality of separate banks of memories with each bank storing a set of correction or compensation coefficients. In this case, each lighting mode use a separate bank and thus a separate set of compensation coefficients. When multiple memory banks are used, a bank switch coupled between processor and the compensation memory allows the processor to select a particular one or ones of the banks of compensation memory. The appropriate memory bank is selected by the processor prior to the time a frame is acquired. In particular, the processor selects particular values in the memory to be used according to which lighting mode will be used.

In one embodiment, the compensation circuit includes a compensation memory coupled to an adder circuit and a multiplier circuit. The image acquisition circuit provides a pixel value (in the form of a digital signal) to a first port of the adder circuit and the compensation memory provides an offset value to a second port of the adder circuit. The adder circuit combines the two values fed thereto and provides a partially compensated pixel value to the input of the multiplication circuit. The multiplication circuit further compensates the pixel value prior to providing the fully compensated pixel value to the video frame memory and the DMA channel.

A further advantage of the present invention is that the cost of illumination hardware can be reduced. As mentioned above, relatively low cost illuminators tend to have worse nonuniformities than relatively expensive illuminators. The present invention, however, makes it possible to tolerate greater irregularity in the illumination, and therefore makes it possible to employ relatively low cost illuminators while still achieving an accuracy which is equivalent to that obtained with relatively high cost illuminators.

In accordance with a further aspect of the present invention, an AOI system includes an image acquisition system having an output port coupled to a first input port of an adder circuit. A second input of the adder circuit is coupled to an offset memory and an output of the adder circuit is coupled to a first input of a multiplier circuit. A second input of the multiplier circuit is coupled to an offset memory and an output of the multiplier circuit has an output coupled to a video frame memory and a DMA channel. The DMA channel is coupled to a processor memory. The processor memory may be provided, for example, either as a main memory in a so-called "motherboard" or as a processor on a frame grabber module which includes bother the frame grabber processor and a frame grabber memory.

With this particular arrangement, an AOI system which corrects pixel values in a digital image on a pixel by pixel basis as the signals representing the video frame are transferred from the image acquisition system to the frame memory is provided. The adder, multiplier and memory circuits operate at a speed which is coefficient to allow the system to compensate pixel values in real time, thus allowing compensated or corrected pixel values to be stored in the memory for later processing.

A further advantage of the present invention is that in the case where the image acquisition system includes both a camera and a digitizer, the invention simultaneously compensates for linear nonuniformities in the camera and in the digitizer as well as for illumination nonuniformity. If the digitizer had a constant offset, for example, that offset would be removed in the calibration process described here.

The digitized pixel values contain signal information from the inspected specimen and error information caused by uneven illumination. The digitized pixel values are presented to the second input of the adding circuit.

The output of the adding circuit is a pixel value which has been corrected for offset. It is presented to the second input of the multiplication circuit. The output of the multiplication circuit is a pixel value which has been corrected for scale and offset.

The addition and multiplication circuits can be implemented in any of several ways known to those skilled in the art of arithmetic circuitry. In the preferred embodiment the adder and multiplier can be generated using Very high speed integrated circuit Hardware Descriptive Language (VHDL) software statements compiled for a programmable gate array.

The correction coefficient memories may be organized in any convenient way. In the preferred embodiment, it is sixteen million sixteen-bit words in which each sixteen-bit word is broken up into eight bits of offset coefficient and eight bits of scale coefficient. Embodiments are envisioned in which fewer bits of offset are used and more bits of scale, or vice versa—this would be appropriate if the variation in offset were small and the variation in scale were large. It might be reasonable in some cases to represent both scale and offset values in a total of eight bits, with three bits for offset and five bits for scale.

Other ways of managing multiple blocks of correction coefficients for multiple lighting modes are contemplated as well. For example, if memory cost were important and lighting modes were infrequently changed, the time of reloading a lighting mode's information would not be important. The bank switch could be eliminated (or set to a constant value) and the entire memory could be reloaded from the computer for each separate lighting mode. This would allow the invention to be realized with smaller memories, but would use time in reloading the memories, as opposed to the much faster bank switch. In the case where only one lighting mode is used, only one memory bank (or one set of memory banks) is needed.

The output of the multiplication circuit is a corrected pixel value—the value the pixel would have had if the illumination had been uniform. The pixel has been corrected for offset and for scale. The corrected value is stored in frame memory in lieu of the original raw digitized pixel, as would have been stored by a conventional framegrabber.

The correction has been made in real time, so the computer can process corrected pixels as fast as if they had not been corrected. No central processor cycles are used in making the correction.

In accordance with a further aspect of the present invention, a method for correcting errors in an AOI system includes the steps of (a) acquiring a frame and digitizing each pixel in the frame, (b) generating an address to indicate where the pixel is to be stored in a video frame memory, (c) retrieving correction values related to the pixel position and (d) combining the correction values with the digitized pixel value to provide a corrected pixel value.

With this particular arrangement, a method for real-time compensation of pixel values in an AOI system is provided. The correction values correspond to offset and scale correction values. The correction values are combined with the pixel values by first adding an offset correction value to the digitized pixel value to provide a partially corrected digitized pixel value and then by multiplying the corrected digitized pixel value by a scale correction value to provide a fully corrected pixel value.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
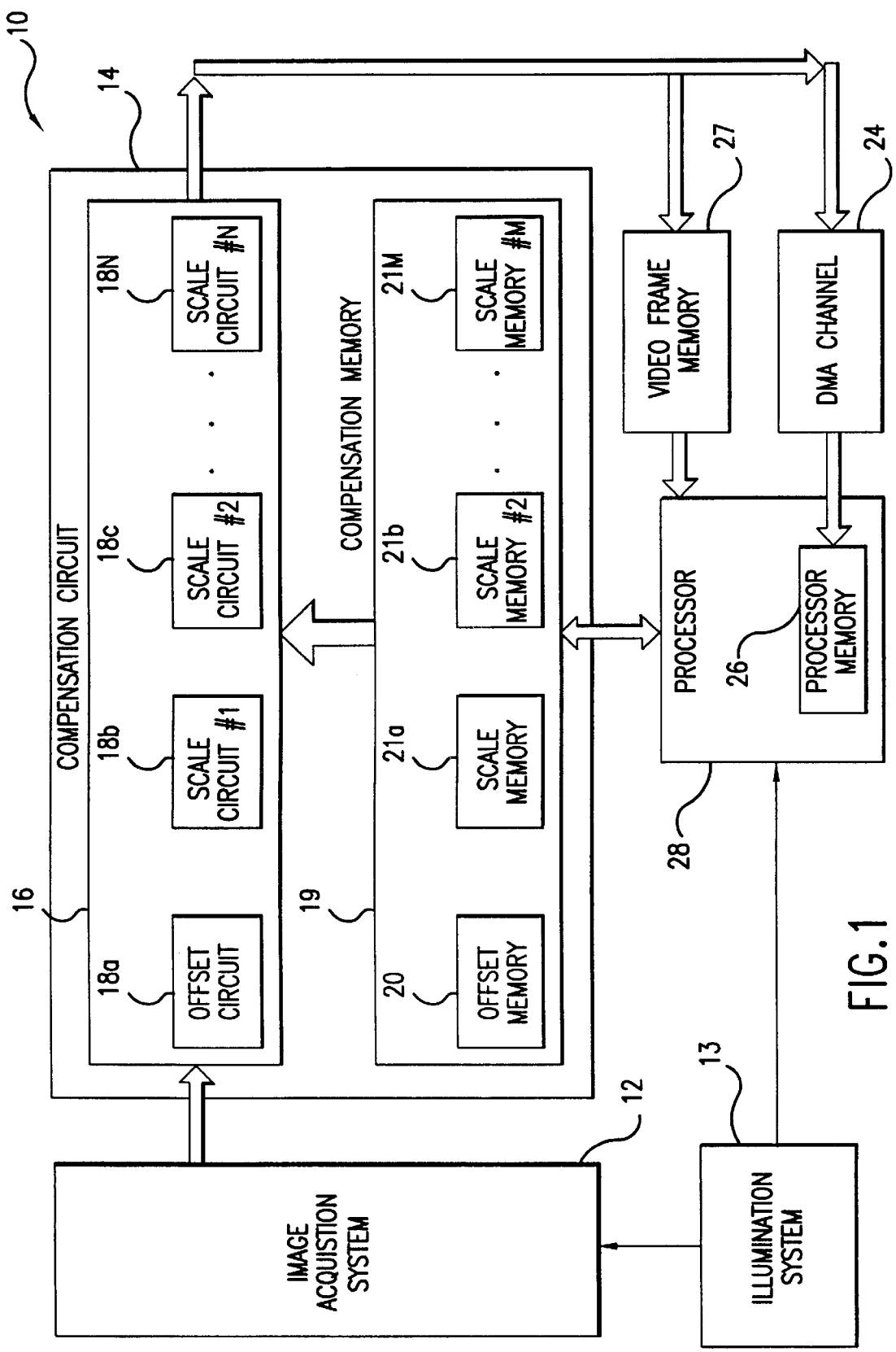
FIG. 1 is a block diagram of an automated optical inspection system which performs correction of images.

Before describing an automated optical inspection (AOI) system in accordance with the present invention, and the operations performed to make corrections due to non-uniform illumination and other non-time varying errors some introductory concepts and terminology are explained.

An analog or continuous parameter image such as a still photograph may be represented as a matrix of digital values and stored in a storage device of a computer or other digital processing device. Thus, as described herein, the matrix of digital data values is generally referred to as a "digital image" or more simply an "image" and may be stored in a digital data storage device, such as a memory for example, as an array of numbers representing the spatial distribution of energy at different wavelengths in a scene.

Similarly, an image sequence such as a scanned view of a printed circuit board, for example, may be converted to a digital video signal as is generally known. The digital video signal is provided from a sequence of discrete digital images or frames. Each frame may be represented as a matrix of digital data values which may be stored in a storage device of a computer or other digital processing device. Thus in the case of video signals, as described herein, a matrix of digital data values are generally referred to as an "image frame" or more simply an "image" or a "frame." Each of the frames in the digital video signal may be stored in a digital data storage device, such as a memory for example, as an array of numbers representing the spatial distribution of energy at different wavelengths in a scene in a manner similar to the manner in which an image of a still photograph is stored.

Whether provided from a still photograph or a video sequence, each of the numbers in the array correspond to a digital word (e.g. an eight-bit binary value) typically referred to as a "picture element" or a "pixel" or as "image data." The image may be divided into a two dimensional array of pixels with each of the pixels represented by a digital word.

Reference is also sometimes made herein to color images with only a luminance component. Such images are known as grey scale images. Thus, a pixel represents a single sample which is located at specific spatial coordinates in the image. It should be noted that the techniques described herein may be applied equally well to either grey scale images or color images.

In the case of a grey scale image, the value of each digital word corresponds to the intensity of the pixel and thus the image at that particular pixel location. In the case of a color image, reference is sometimes made herein to each pixel being represented by a predetermined number of bits (e.g. eight bits) which represent the color red (R bits), a predetermined number of bits (e.g. eight bits) which represent the color green (G bits) and a predetermined number of bits (e.g. eight bits) which represent the color blue (B-bits) using the so-called RGB color scheme in which a color and luminance value for each pixel can be computed from the RGB values. Thus, in an eight bit color RGB representation, a pixel is represented by a twenty-four bit digital word.

It is of course possible to use greater or fewer than eight bits for each of the RGB values. It is also possible to represent color pixels using other color schemes such as a hue, saturation, brightness (HSB) scheme or a cyan, magenta, yellow, black (CMYK) scheme. It should thus be noted that the techniques described herein are applicable to a plurality of color schemes including but not limited to the above mentioned RGB, HSB, CMYK schemes as well as the Luminosity and color axes a & b (Lab), YUV color difference color coordinate system, the Karhunen-Loeve color coordinate system, the retinal cone color coordinate system and the X, Y, Z scheme.

Reference is also sometimes made herein to an image as a two-dimensional pixel array. An example of an array size is 512 pixels×512 pixels. One of ordinary skill in the art will of course recognize that the techniques described herein are applicable to various sizes and shapes of pixel arrays including irregularly shaped pixel arrays.

An image region or more simply a region is a portion of an image. For example, if an image is provided as a 32×32 pixel array, a region may correspond to a 4×4 portion of the 32×32 pixel array.

Referring now to FIG. 1, an automated optical inspection (AOI) system 10 includes an image acquisition system 12 which obtains analog or continuous parameter images of a specimen to be inspected. The specimen is illuminated by an illumination system 13. The image acquisition system 12 provides a digital signal (e.g. a stream of digital bits) to a compensation circuit 14.

The compensation circuit 14 includes a compensation function circuit 16 coupled to a compensation memory circuit 19. The compensation memory circuit 19 has stored therein compensation values which are provided to the compensation function circuit 16. The compensation function circuit 16 receives the compensation values and appropriately applies them to pixel value being provided thereto from the image acquisition system 12. The compensation values stored in the compensation memory 19 can be generated via a system calibration technique such as the techniques described below in conjunction with FIGS. 3 and 4.

The compensation function circuit 16 includes one or more compensating circuits 18a—18N generally denoted 18. In FIG. 1, compensating circuit 18a corresponds to an offset circuit 18a and compensating circuits 18b–18N correspond to scale circuits 18b–18N. Although only one offset circuit is here shown, it should be noted that in some embodiments, it may be desirable to use more than on offset circuit. The operation of the offset and scale circuits 18a–18N will be described in detail below. Suffice it here to say that the offset circuit 18a and scale circuits 18b–18N receive compensation values from the compensation memory 19 and apply the compensation values to pixel values received from the image acquisition system 12. The compensation circuit 14 thus corrects for errors due to non-uniform illumination and other errors.

The compensation memory 19 can be provided from a single memory or a bank of memories. In FIG. 1, compensation memory 19 is shown provided from a plurality of memories 20a and 21a–21M. In this particular embodiment, the memory 20 is provided as an offset memory and memories 21a–21M are provided as scale memories.

It should be appreciated that each of the individual memories 20 and 21a–21M could comprise a bank of memories with each of the different memory banks have different compensation values stored therein. For example, a first bank of memory 20 can hold compensation values to be used for a first lighting mode and a second different bank of memory 20 can hold compensation values used for a second different lighting mode. The particular bank of offset memory 20 selected for use during an inspection process depends upon the lighting mode being used in the system. When the system is operating in the first lighting mode, the first memory bank of offset memory 20 is used and when the system is operating in the second lighting mode, the second memory bank of offset memory 20 is used. Thus, different compensation values can be used for each lighting mode. Banks of scale memories 21a–21M could operate in a similar manner.

Although, N scale circuits 18b–18N are shown in FIG. 1, those of ordinary skill in the art will appreciate that one or more scale circuits 18b–18N could be used. Similarly, although, M scale memories 21a–21M are shown in FIG. 1, those of ordinary skill in the art will appreciate that one or more scale memory circuits could be used. Each of the one or more offset memories and scale memories provide compensation values to one or more of the offset and scale circuits.

After the compensation circuit 14 compensates the pixel values from the image acquisition circuit 12, the compensated pixels values are transmitted from the compensation circuit 14 to a memory for storage.

In one embodiment, the compensated pixels values are transmitted from the compensation circuit 14 through a direct memory access (DMA) channel 24 to a memory 26 of a processor 28. The processor 28 may be provided, for example, as a general purpose computer, an image processing processor or any other type of processor capable of processing image information and performing all or portions of an inspection process.

It should be appreciated, however, that other embodiments are also possible. For example, in another embodiment, the system can include a frame grabber module. The frame grabber module could include the processor 28 and the memory 26. In this case, the memory 26 would correspond to a video frame memory 26 on the frame grabber module. Thus, in this embodiment, the DMA channel 24 is coupled between the compensation circuit 14 and the frame grabber module (which includes the processor 28 and the video frame memory 26) and corrected pixel values are transferred via a DMA process directly from the compensation circuit 14 to the frame grabber module memory 26.

In still another embodiment, a frame grabber module could include a video frame memory (illustrated as video frame memory 27 in FIG. 2) and the processor 28 can be provided as part of a module separate from but coupled to the frame grabber module. Thus, in such an embodiment, the frame grabber module is couple between the compensation circuit 14 and the processor 28 and corrected pixel values are transferred directly from the compensation circuit 14 to the frame grabber module memory (illustrated as video frame memory in 27 in FIG. 1) and subsequently accessed by the processor 28. Thus, in this case, the DMA channel 24 can be omitted.

In operation, prior to frame acquisition, the processor 26 selects particular memory addresses in which compensation values for particular pixel regions are stored. It should be appreciated that to compensate the pixel values in real time, it is necessary to provide at least one memory with correction information in it. Thus, the compensation memory 19 (e.g. the memories 10 and 21a–21M) have stored therein compensation values for particular pixel regions.

The correction is performed pixel by pixel as the signals representing the video frame are being transferred from the image capture system 12 though the compensation circuit 14 and to the video frame memory 27 or DMA channel 24. Compensating the pixels for irregularities in real time makes it possible to continue processing video information at the same rate as without correction.

It should be understood by those of ordinary skill in the art, that the details of the architecture of the compensation memory 19 vary with the nature of the aberrations expected. For example, if a pure linear correction with no offset errors is expected, then the error values can be represented mathematically as y=mx, where m corresponds to the scale factor. Thus, in this case, the compensation memory 19 can be provided from a single scale memory (e.g. memory 21a).

On the other hand, if a pure linear correction with an offset error is expected, then the error values can be mathematically represented as y=mx+b, where m corresponds to the scale factor and b corresponds to the value of the offset. In this case, the compensation memory 19 can be provided from a single scale memory (e.g. memory 21a) and an offset memory (e.g. offset memory 20a which includes, for example, compensation values to eliminate the effete of unexcludable stray light). If a nonlinear correction is needed, more memories (e.g. scale memories 21a–21M) and more compensation function circuits (e.g. compensation function circuits 18a–18N) may be needed. Thus, the compensation scheme of the present invention can be extended beyond simple linear calculations or can be reduced to simpler linear multiples without offset correction.

It should be appreciated that compensation circuit 14, memory 26 and processor 28 may be provided as part of a general purpose computer properly programmed to perform the functions of all of the above circuits.

Figure 2:
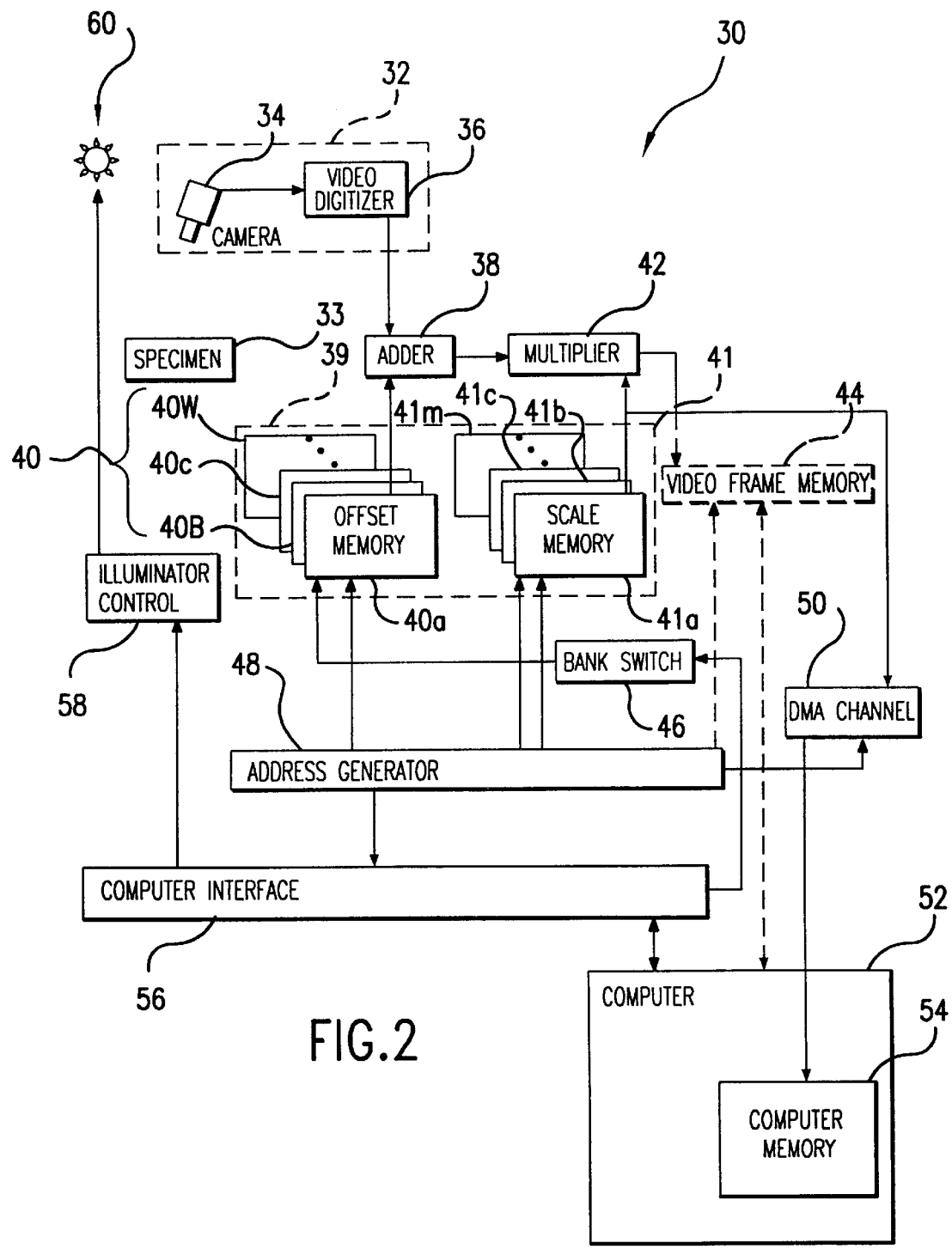
FIG. 2 is a block diagram of an automated optical inspection system which includes an offset memory and a scale memory for use in performing correction on a pixel by pixel basis as the signals representing the video frame are being loaded into frame memory from a camera.

Referring now to FIG. 2, an automated optical inspection (AOI) system 30 includes an image acquisition system 32 which obtains analog or continuous parameter images of a specimen 33 to be inspected. The image capture system 32 may be provided, for example, as a digital camera (i.e. a camera which captures an analog input signal and provides a digital signal output). Alternatively, as shown in FIG. 2, the image acquisition system 32 may also be provided from a camera 34 having a video digitizer 36 coupled thereto. The video digitizer 36 receives analog signals from the camera 34 and provides digital signals at an output thereof In the embodiment, shown in FIG. 2, the camera 34 obtains a new image frame every 1/60 seconds. Those of ordinary skill in the art will appreciate of course that cameras which obtain new image frames at speeds greater or less than 1/60 seconds may also be used.

The video digitizer 36 receives the analog signal from the camera 34, samples the analog signal, converts the analog signal into a stream of bits and provides a digital signal at an output thereof Thus, in this manner, each pixel of every image obtained by the camera 34 is digitized.

Each of the freshly digitized pixel values, which contain signal information from the inspected specimen 33 and error information caused by uneven illumination, are presented to a first input of an adder circuit 38. Error information can be generated, for example, by stray light which reaches the inspection or calibration area or pixel sensitivity variations across a camera detector (e.g. a CCD, a CMOS detector of any other type of detector suitable for use in an image acquisition system.

A correction coefficient memory 39, having correction coefficient values stored therein comprises a bank of offset memories 40a—40N and a bank of scale memories 41a–41M. The correction coefficient memory 39 is coupled to a second input port of the adder circuit 38.

When a pixel is transferred from the image acquisition system 32 to the first input of the adder 38, a selected one of the offset memories 40a–40N provides an offset value to the second port of the adder 38. It should be appreciated that the pixel values can be transferred from the selected one of the offset memories 40a–40N to the second port of the adder circuit 38 either before, after or at the same time the pixel value is transferred from the image acquisition system to the second port of the adder circuit 38. The particular one of the offset memories 40a–40N which is selected is determined in a manner described below. The adder 38 combines the values provided to the first and second inputs and provides a corrected offset digitized pixel value to a first input of a multiplier circuit 42. Thus, the output of the adding circuit 38 is a pixel value which has been corrected for offset. It is presented to a second input of the multiplication circuit 42.

The second port of the multiplier circuit 42 is coupled to the correction coefficient memory 39. In particular, a selected one of the scale memories 41a–41M provides a scale correction value to the second input of the multiplier circuit 42. It should be appreciated that the pixel values can be transferred from the selected one of the scale memories 41a–41M to the second port of the multiplier circuit 42 either before, after or at the same time the pixel value is transferred from the adder circuit 38 to the second port of the multiplier circuit 42.

The multiplier circuit 42 provides a corrected pixel value (i.e. the value the pixel would have had if the illumination had been uniform) at an output thereof The pixel has been corrected for offset and for scale.

As mentioned above, in the embodiment of FIG. 2, the offset memory 40 is provided from a bank of memories 40a—40N and the scale memory 41 is provided from a bank of memories 41a–41M. Each of the different offset memory banks 40a–40N have different compensation values stored therein. The inspection system 30 operates in a plurality of different lighting modes. Depending upon the particular lighting mode being used, the compensation values are selected from a predetermined one of the offset memories 40a–40N. For example, offset memory bank 40a can hold compensation values used for a first lighting mode and offset memory bank 40b can hold compensation values for a second different lighting mode. The particular compensation values used during an inspection process thus depends upon the lighting mode being used in the system.

Similarly, each of the different scale memory banks 41a–41N have different compensation values stored therein. Depending upon the particular lighting mode being used, the compensation values are selected from a predetermined one of the scale memories 41a–41N. For example, scale memory bank 41a can hold compensation values used for a first lighting mode and offset memory bank 41b can hold compensation values for a second different lighting mode.

The output of the multiplier circuit 42 is coupled to a DMA channel 50 through which the corrected pixel data is transferred to a memory 54 of an image processing computer 52. The transfer is made via a DMA process. The computer 52 may be provided, for example, as a general purpose computer, an image processing processor or any other type of processor capable of processing image information and performing all or portions of an inspection process.

It should be appreciated, however, that other embodiments are also possible. For example, in another embodiment, the processor 52 and memory 54 could be provided as part of a frame grabber module. Thus, in this embodiment, the DMA channel 24 would be coupled between the multiplier circuit 42 and the frame grabber module (which includes the processor and memory 54).

In still another embodiment, a frame grabber module could include a video frame memory (illustrated in phantom as video frame memory 44 in FIG. 2) and the processor 52 can be provided as part of a module separate from but coupled to the frame grabber module. Thus, in such an embodiment, the video frame memory 44 of the frame grabber module is coupled between the multiplier circuit 42 and the processor 52 and corrected pixel values are transferred directly from the multiplier circuit 42 to the video frame memory 44 of the frame grabber module and subsequently accessed by the processor 52. Thus, in this case, the corrected value is stored in the video frame memory 44 in lieu of the original raw digitized pixel, as would have been stored by a conventional framegrabber and the DMA channel 24 can be omitted.

A bank switch 46 coupled between a computer interface and the memory 39 allows the computer to select the appropriate one of the several memory banks 40a–40N and 41a–41M Prior to frame acquisition time, the computer 52 selects appropriate ones of the banks 40a–40N and 41a–41M.

An address generator 48 is coupled to the correction coefficient memory and to the DMA channel 50 (or the video frame memory 44 in the embodiments which include the video frame memory and omit the DMA channel). The address generator 48 is also coupled to a computer interface 56 which in turn is coupled to an illuminator control 58. The illuminator control 38 controls an illumination source 40 during the calibration process and implements different lighting modes.

The address generator 48 generates an address to activate the video frame memory 44 in which the pixel is to be stored. The address indicates where the corrected digitized pixel value is to be stored in the video frame memory 44. The address generator 48 also activates the offset and scale factor memories 40a, 40b in the selected bank.

In operation in a first lighting mode, in response to the address generator 48, the offset correction value is retrieved from the offset memory 40a and presented to a first input of the adding circuit 38. The adding circuit 38 adds the offset value to the pixel value to provide a corrected offset pixel value. Also in response to the address generator 48, the scale correction is retrieved from the scale memory 41a and presented to a first input of a multiplication circuit 42. The multiplication circuit 42 multiplies the offset corrected pixel value by the scale correction value. In an embodiment which includes a DMA channel, the resultant corrected pixel value is transmitted to the processor and memory 52, 54 through the DMA channel 50. In an embodiment which does not include a DMA channel, the resultant corrected pixel value is transmitted to the video frame memory 44 and accessed by the processor 52. In either case, the correction has thus been made in real time, so the computer 52 can process corrected pixels as fast as if they had not been corrected. It should be noted that no central processor cycles are used in making the correction with the technique of the present invention.

A computer interface 56 is coupled between the computer 52 and an illumination control 58 which in turn is coupled to an illuminator 60. The illuminator control 58 is used to control (e.g. vary) the intensity and/or flash duration of the illuminator 60. This is done to generate variable lighting modes during use and during calibration.

It should be appreciated that the correction coefficient memory 39 may be organized in any convenient way. In a preferred embodiment, it is sixteen million sixteen-bit words in which each sixteen-bit word is broken up into eight bits of offset coefficient and eight bits of scale coefficient which are stored in offset and scale memories 20a, 20b, respectively. In some embodiments, however, it may be desirable to use fewer bits of offset and more bits of scale, or vice versa. Such modifications may be desirable or even necessary if the variation in offset were small and the variation in scale were large, for example. It might be reasonable in some cases to include both scale and offset values in eight bits, with three bits used to represent an offset value and five bits used to represent a scale value.

Other ways of managing multiple blocks of correction coefficients for multiple lighting modes are contemplated as well. For example, if memory costs were important and lighting modes were infrequently changed, the time of reloading a lighting mode's information would be important. In this case, the bank switch 46 could be eliminated (or set to a constant value) and the entire memory 39 could be reloaded from the computer 52 for each separate lighting mode. This would allow the calibration technique to be realized with smaller memories, but would use time in reloading the memories, as opposed to the much faster bank switch 46.

It should also be appreciated that the addition and multiplication circuits can be implemented in any of several ways known to those skilled in the art of arithmetic circuitry. In a preferred embodiment, the adder and multiplier circuits 38, 42 are generated using VHDL software statements compiled for a programmable gate array.

Likewise, the adder 38, memory 39, multiplier 42 switch 46 and address generator may be provided as part of a general purpose computer properly programmed to perform the functions of all of the above circuits. In short, the camera 34 could provide image signals to a properly programmed general purpose computer which would then perform all of the calibration and inspection steps described above in conjunction with FIGS. 1 and 2.

It should further be appreciated that in this exemplary embodiment of the inspection system, the image acquisition system 32 does not store the image in a local memory (e.g. video frame memory 44). Rather, the image is placed in the computer's main memory through the DMA channel 50. It should thus be appreciated that the addresses generated by the DMA channel 50 may not be identical to those of the offset and scale memories 40a, 40b. The physical addresses in the memory 54 may not even be contiguous, depending upon the memory management scheme employed in the computer 52. Thus, in order for accurate corrections to be made to correct the pixel, there must be coordination between the address generator for the offset and scale memories and the addressing sequence of the DMA channel 50.

Also, in the embodiment shown in FIG. 2, the correction is performed pixel by pixel as the signals representing the video frame are being transferred from the camera 34 though the compensation circuits 38, 42 and to the video frame memory 44 or the DMA channel 50. Compensating the pixels for irregularities in real time makes it possible to continue processing video information at the same rate as without correction. Thus, the time it takes for the frame data to be transmitted from the camera 14 output to the frame memory 44 or DMA channel must be no greater than the speed at which the camera captures a frame (e.g. 1/60 sec.).

Figure 3:
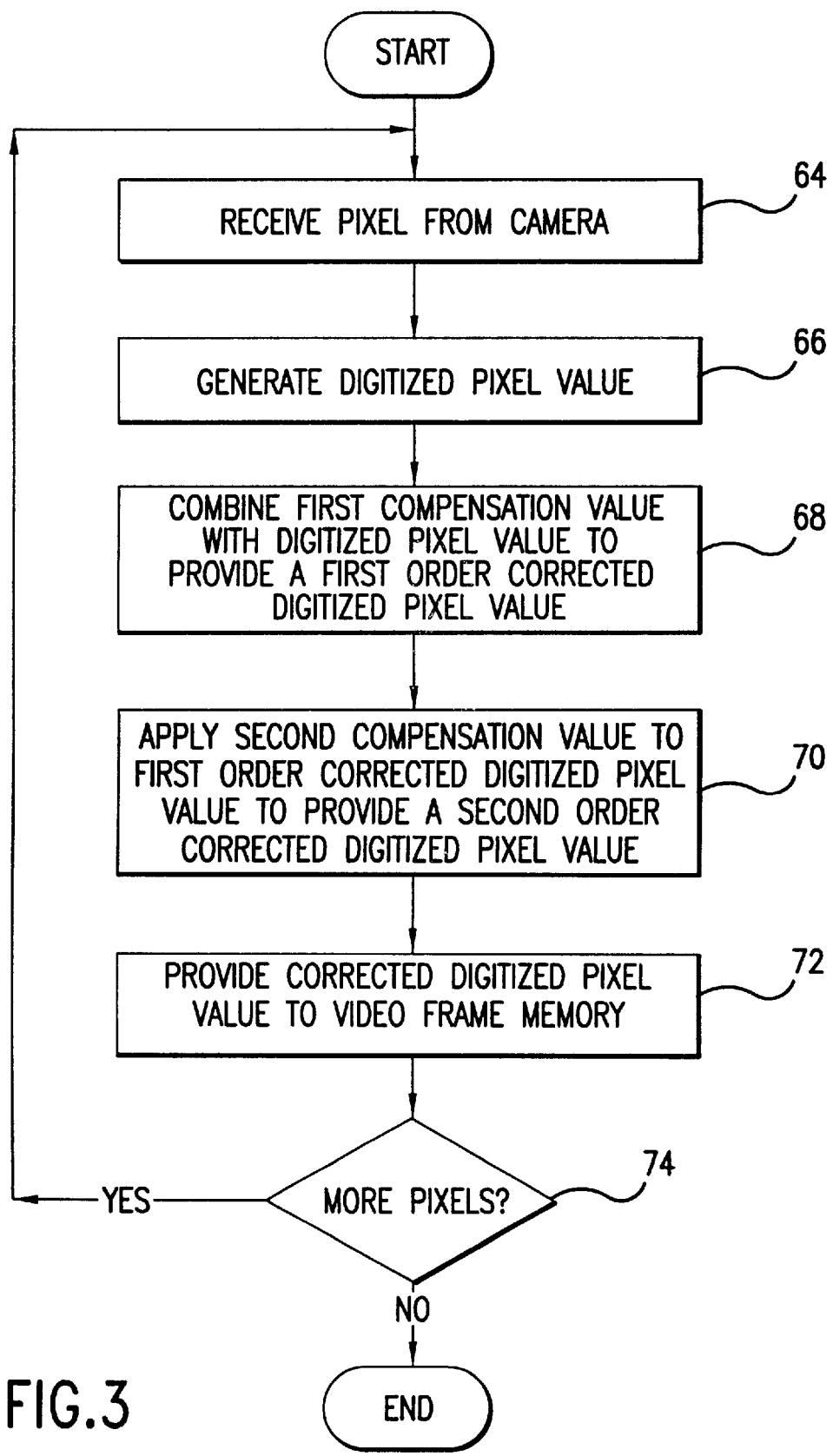
FIG. 3 is a flow diagram of a method to perform real time compensation.
Figure 4:
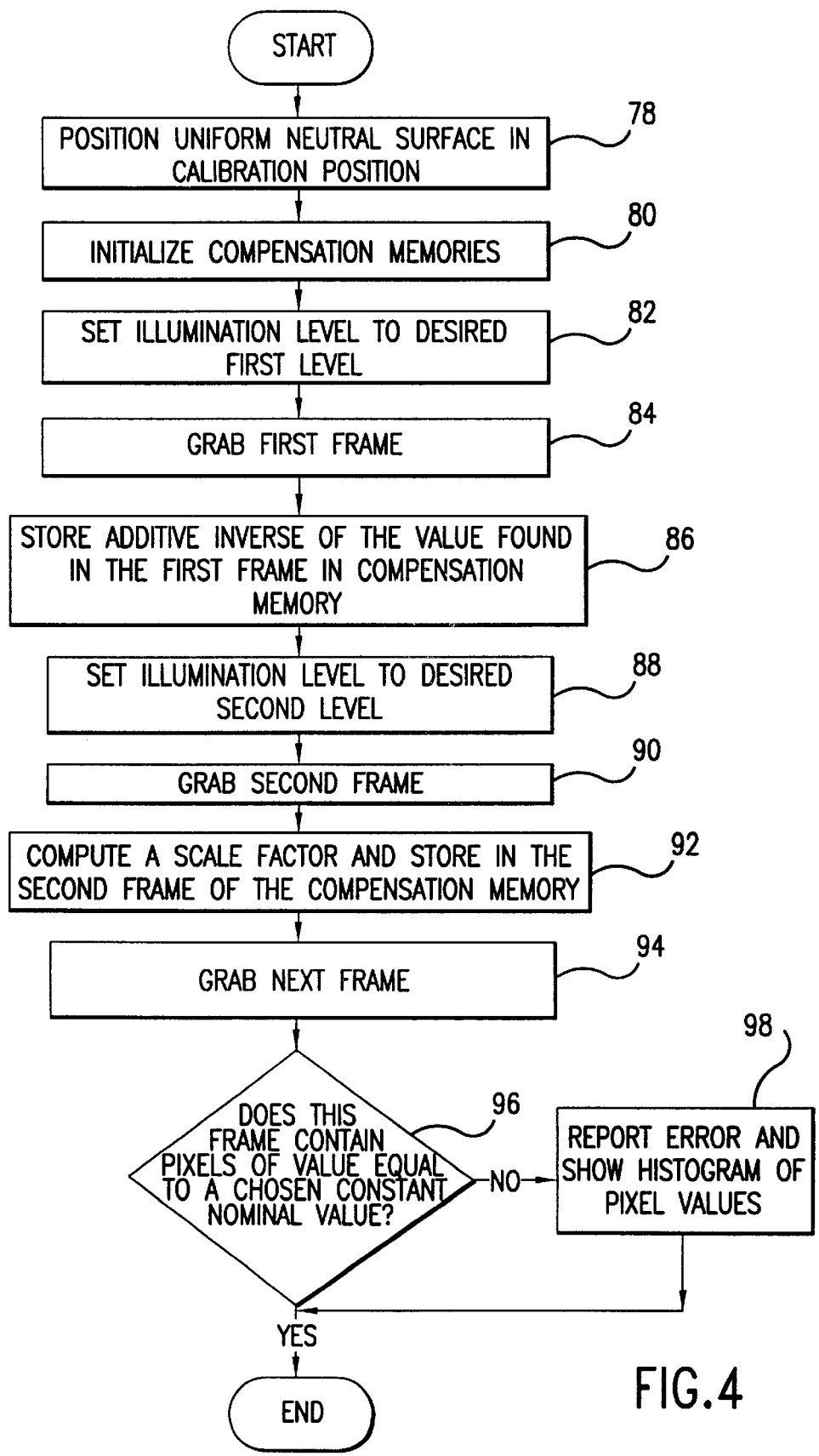
FIG. 4 is a flow diagram of a method for determining compensation values.

FIGS. 3 and 4 are a series of flow diagram showing the processing performed by a processing apparatus which may, for example, be provided as part of an AOI system such as that shown in FIG. 1. The rectangular elements (e.g. block 64 in FIG. 3) in the flow diagram(s) are herein denoted "processing blocks" and represent steps or instructions or groups of instructions. Some of the processing blocks can represent an empirical procedure or a database operation while others can represent computer software instructions or groups of instructions. The diamond shaped elements in the flow diagrams (e.g. block 74 in FIG. 3) are herein denoted "decision blocks" and represent steps or instructions or groups of instructions which affect the processing of the processing blocks. Some of the decision blocks can also represent an empirical procedure or a database operation while others can represent computer software instructions or groups of instructions. Thus, some of the steps described in the flow diagram may be implemented via computer software while others may be implemented in a different manner e.g. via an empirical procedure.

Alternatively, some of the blocks can represent steps performed by functionally equivalent circuits such as a digital signal processor circuit or an application specific integrated circuit (ASIC). Alternatively, still all of the blocks in FIGS. 3 and 4 can represent steps performed by a properly programmed general purpose computer or processor.

The flow diagram does not depict the syntax of any particular programming language. Rather, the flow diagram illustrates the functional information one of ordinary skill in the art requires to perform the steps or to fabricate circuits or to generate computer software to perform the processing required of the particular apparatus. It should be noted that where computer software can be used, many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention.

Turning now to FIG. 3, processing begins with steps 64 and 66 in which a pixel is received from a camera and a digitized pixel value is generated. These operations are familiar to anyone skilled in the art of designing video frame grabbers.

In step 68, a first compensation value is combined with the digitized pixel value generated in step 66 to provide a first order corrected digitized pixel value. In one embodiment (e.g. an embodiment such as that shown in FIG. 2), the first compensation value is provided as an offset correction value. In this case the offset correction value is combined with the digitized pixel value to provide an offset corrected digitized pixel value.

In some applications, it may only be necessary to provide a first order correction. Thus, in this case no other corrections to the digitized pixel values are required. In other applications, however, further correction of the digitized pixel values may be desired or warranted. In this case, processing proceeds to step 70.

In processing step 70, a second correction value is applied to the first order corrected digitized pixel value to provide a second order corrected digitized pixel value. In the system of FIG. 2, for example, the second correction value is provided as a scale correction value which multiplies the corrected offset digitized pixel value to provide a corrected digitized pixel value.

It should be appreciated that in some applications only a single correction will be necessary and thus either of steps 68 or 70 may be omitted. That is, in some applications only the first correction value would be used while in other applications only the second correction value will be used.

Processing then proceeds to step 72 in which the corrected digitized pixel value is provided to video frame memory where the corrected digitized pixel value is then available for further processing by an image processor for example.

Processing then proceeds to decision block 74 where decision is made as to whether more pixels remain to be processed. If no additional pixels remain to be processed, then processing ends. If, on the other hand, additional pixels remain to be processed, then processing returns to step 64 where the next pixel is received by the camera and steps 66–74 are repeated until no more pixels remain to be processed.

It should be noted that before this system can be used, offset and scale memories (e.g. memories 40 and 41 in FIG. 2) must be filled with appropriate values. During machine operation, the offset and scale memories 40 and 41 will normally be filled from files recorded in mass storage such as disk or flash memory.

Obtaining the correction coefficients in the first place requires a calibration procedure. In one calibration procedure, a camera to be corrected with its illuminator is aimed at a uniform neutral surface such as a gray card or a white card. Uniform neutral media can be obtained from a number of sources supplying the photography and optical trade and known to those skilled in the art of photometry and photography. A number of exposures of the chosen uniform neutral surface are taken at different intensities or flash durations which can be achieved via an illuminator control (e.g. illuminator control 58 in FIG. 2). Another calibration procedure for automatically obtaining correction coefficients is described below in conjunction with FIG. 4.

The number of exposures taken in a calibration process must be sufficient to provide enough data to calculate all necessary pixel correction coefficients for each pixel. For example, if only scale is to be corrected, a single exposure is sufficient. If scale and offset are to be corrected, two exposures at different illumination values will be required. Suitable arithmetic will be performed on each pixel value in order to separate the effects of offset and scale. If the corrections to be performed are other than straight line offset and scale, more than two sets of coefficients will likely be required, and more than two calibrating exposures will also be require. The number of coefficients is particular to the kind of compensation function being used. If more than two coefficients are needed per pixel, then more than the two memories shown in the drawing will also be required.

In a preferred embodiment, linear scale and offset are corrected, and thus two memories are used (e.g. memories 40 and 41 in FIG. 2), and two calibration exposures are performed. One exposure is taken at a low or zero value of illumination and one at an illumination value known not to saturate any pixel. In practice, saturation can be detected automatically and its effects eliminated. Methods of detecting saturation and backing off from it are well known to those of ordinary skill in the art.

In a preferred embodiment, both "raw frames" (i.e. the dark and bright frames) are transferred without compensation to arrays in central computer memory. It should be noted that any memory architecture capable of presenting the data to a processing unit could be used. The first pixel array is designated Pdark[0 . . . N] and the second pixel array is designated Pbright[0 . . . N]. The pixel arrays Pdark and Pbright are used to calculate two other arrays Scale[0 . . . N] and Offset[0 . . . N]. The variable 0 . . . N represents not only a memory address but also a physical location in the field of view. If the illumination were truly uniform and the camera truly perfect, all the Pdark values would be zero, and all the Pbright values would be equal to each other and less than the saturation value. In this ideal case, all Scale values would be equivalent to unity, and all Offset values would be zero.

In practice, however, the Pdark values are not all zero, perhaps because the illuminator cannot be fully turned off, or there is stray light which cannot be shut out. Some pixel offsets may be negative, and others positive. The Pbright values are not all equal, because the illuminator is not uniform. A preferred embodiment of the invention corrects both of these sources of nonuniformity at the same time, provided a linear model describes the aberrations.

According to the earlier description, each incoming pixel will be added to the contents of the Offset memory and the result of the addition will be multiplied by the contents of the Scale memory, i.e.

$$\text{Truepixel}(n) = \text{Scale}(n) * (\text{rawpixel}(n) + \text{Offset}(n))$$

The corrected pixel value Truepixel(n) is the provided to the appropriate memories and DMA channel.

Referring now to FIG. 4, a process for learning the scale and offset values stored in a compensation memory (e.g. compensation memory 19 in FIG. 1 or memories 39, 40a, 40b in FIG. 2) I shown. In a preferred embodiment, a processor learns the scale and offset values for each pixel by utilizing an automatic process as next described.

Processing begins with step 78 in which a uniform neutral surface is positioned in a calibration position. The neutral surface may be provided, for example, as a white card or a gray card (e.g. an eight inch by ten inch gray card with 18% density of the type manufactured by Eastman Kodak and referred to as Kodak Publication No. R-27).The calibration position is a position normally occupied by the specimen to be measured and is within a field of view of the image acquisition and illumination systems.

Next as shown in step 84 the compensation memory is initialized. It should be appreciated by those of ordinary skill in the art that in the case where the compensation memory is provided as separate memories (e.g. by partitioning a single physical memory or by utilizing physically separate memories) all of the memories should be appropriately initialized. In the AOI system of FIG. 2, for example, all cells of the offset memory 40a should be set to zero and all cells of the scale memory 40b should be set to unity.

Processing next proceeds to step 82 in which an illumination level is set to a first desired level to provide a particular illumination characteristic to the uniform neutral surface which is positioned in the calibration position. In one particular embodiment, the illumination level is set to zero meaning that no illumination is provided. In step 84, a first image frame is acquired or "grabbed." In the case where the first desired level corresponds to zero, the first frame corresponds to a "dark" frame. At the point, the pixel values in the first frame are uncompensated and ideally all pixel values in this frame should be zero. In practice, however, some of the pixel values in the dark frame are nonzero values. The nonzero values are due to offsets caused primarily by non-uniform or stray illumination of the neutral surface.

In step 86, the additive inverse of the value found in the first frame is stored in the compensation memory. In practice, this may be accomplished by first storing the measured values in a temporary array of pixels, computing the inverse of the measured values and then storing this array in a mass storage file for future use.

The array of additive inverse values is also be stored in the offset memory (e.g. offset memory 40a in FIG. 1) for immediate use. The offset memory 40a now contains sufficient information to correct the next grabbed frame for offset values.

Next in step 88, the illumination level is set to a desired second level to provide a second particular illumination characteristic to the uniform neutral surface which is positioned in the calibration position. In the case where the first illumination level was set to zero, the second illumination level preferably corresponds to the brightest non-saturating level contemplated for use.

It should be appreciated that the order of the lighting levels are used during calibration could be reversed (e.g. use bright level first and dark level second).It is also possible to use other lighting levels besides bright and dark.

In step 90, a second image frame is acquired or "grabbed." In the case where the second desired level corresponds to the brightest non-saturating level contemplated for use zero, the second frame corresponds to a "bright" frame. The pixel values are again "raw" and ideally all pixel values in this frame should have a value of one. In practice, however, some of the pixel values in the bright frame are not equal to one. Because all pixel values are compensated for offset, all pixel value variations in this frame are presumed to be due to intensity aberrations in the illumination field. This is due to offsets caused by non-uniform illumination of the neutral surface. Also, optics can lead to nonuniformities because more light passes through the center of an path than the sides and variations across a detector field of view or optical system of a camera can lead to nonuniformities. It should be noted that when grabbing the bright frame, a check is made to determine whether any pixels are saturated. If any are, then the illumination is reduced and another frame is grabbed. It is preferable to process a pixel values which are not in saturation since this results in a linear system while processing of pixel values which are in saturation results in a non-linear system. While it is possible to calibrate using saturated values, it is more efficient in terms of time and computational efficiency to process a linear system.

In step 92, for each location in a temporary array of pixels, a scale factor is calculated. The scale factor will, when multiplied by the bright-frame offset-corrected pixel value, result in a constant nominal value. The constant nominal value must be less than the arithmetic processing limit of the data type being used. In a preferred embodiment, the data type is an unsigned eight bit integer, and the constant value is two hundred. Other embodiments may use different data types and different constant values, if appropriate, without departing from the spirit of the present invention. The values from the temporary array are stored in a mass-storage device for future use and are also stored in a scale memory (e.g. scale memory 40b in FIG. 2) for immediate use.

Processing then proceeds to processing step 94 and decision block 96 in which a next frame is grabbed and a decision is made as to whether that frame contains pixels of value equal to the chosen constant nominal value (in the example given above, this corresponds to a value of two hundred).

If decision is made that the frame does not contain pixels of value equal to the chosen constant nominal value, then an error is reported as shown in step 98. If decision is made in step 96 that the frame does contain pixels of value equal to the chosen constant nominal value, then processing ends.

It should be appreciated that in an automatic optical inspection machine for inspecting printed circuit boards at the time of assembly, an inspection program may have several different lighting modes. For example, different lighting modes may be used to light a specimen being inspected from different angles in order to accentuate or wash out certain features. In each lighting mode, some of the available lighting elements are turned on and others are turned off. It should be noted that the shape of the light distribution may be different for each lighting mode, since each lighting mode uses a different combination of lights, and each different light possibly has is own individual distribution.

In a preferred embodiment of the present invention, the lighting system is a dome having numerous light-emitting diodes all aimed at the specimen but separately controlled, similar to the dome described in U.S. Pat. Nos. 5,060,065 and 5,254,421. To the extent that one lighting mode's intensity distribution differs substantially from another's, it will be necessary and useful to prepare a separate set of correction coefficients for each separate lighting mode. Having prepared the various sets of correction coefficients, it is also necessary to bring each set into play at the time when its corresponding lighting mode is in use.

The various sets of correction coefficients can be brought into play at the time when its corresponding lighting mode is in use by using, for example, a bank switch (e.g. bank switch 46 in FIG. 2). The bank switch could be a distinct item (as shown in FIG. 2) or could simply be an extension of an address generator (e.g. the address generator 48 in FIG. 2). The bank switch is set to zero for lighting mode zero, one for lighting mode one, and so forth up to thirty-two (the number thirty-two is arbitrary and could in practice be larger or smaller than thirty-two without violating the spirit of this invention). Since each picture in one embodiment is 640 by 480 pixels, it consumes in round numbers half a million addresses, and the memory storing correction coefficients must be large enough to store all the coefficients needed for half a million pixels. Thirty two banks of a half million addresses each occupy 16 million addresses.

It should be understood by those of ordinary skill in the art that the correction being applied in the preferred embodiment is a linear one involving an offset and a scale factor. There are many different ways of computing the offset and scale without departing from the spirit of the invention.

It should also be appreciated by those of ordinary skill in the art that a nonlinear compensation could be provided as well, using any of a number of well known polynomial, piecewise-linear, tabular or function-based compensation functions. It is understood that the real-time arithmetic functions could take many forms, and working implementations could easily be formulated by one of ordinary skill in the art of framegrabber design. The specific realization of the circuits and software must operate in real time, providing arrays of corrected frame pixel values ready for immediate analysis by the a processor.

One advantage of the present invention is that the cost of illumination hardware can be reduced. Relatively low cost illuminators tend to have worse nonuniformities than relatively expensive illuminators. The present invention makes it possible to tolerate greater irregularity in the illumination, and therefore makes it possible to employ relatively low cost illuminators while still achieving an accuracy which is equivalent to that obtained with relatively high cost illuminators.

A further advantage of the present invention is that in the case where the image acquisition system includes both a camera and a digitizer, the invention simultaneously compensates for linear nonuniformities in the camera and in the digitizer as well as for illumination nonuniformity. If the digitizer has a constant offset, for example, that offset would be silently removed in the calibration process described herein.

Having described preferred embodiments of the invention, it will now become apparent to one of ordinary skill in the art that other embodiments incorporating their concepts may also be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A system for compensating pixel values in a printed circuit board inspection machine, the system comprising:
   an image acquisition system for digitizing a pixel representing at least a part of the printed circuit board to provide a digitized pixel value at an output of the image acquisition system;
   a compensation circuit coupled to the output of said image acquisition system and comprising a compensation memory having compensation values stored therein, and a compensating circuit, said compensating circuit comprising an offset correction circuit and a scale correction circuit coupled to said offset correction circuit, said compensating circuit having a first port coupled to said image acquisition system having a second port coupled to said compensation memory and having an output port coupled to said means for transferring, said compensating circuit for combining the digitized pixel value received from said image acquisition circuit at the first port with at least one compensation value received from said compensation memory at the second port to provide a compensated digitized pixel value at the output port;
   a memory for storing the compensated digitized pixel value; and
   means for transferring the compensated digitized pixel value between said compensation circuit and said memory.

2. The system of claim 1 wherein said compensation memory comprises:
   a plurality of memory banks each of the memory banks adapted to store a separate set of compensation values.

3. The system of claim 2 further comprising:
   an illumination system for illuminating the printed circuit board in a plurality of different lighting modes with each memory bank adapted to hold a set of compensation values for at least one particular lighting mode.

4. The system of claim 3 further comprising a processor coupled to said memory, said processor for accessing the compensated digitized pixel value stored in said memory.

5. The system of claim 3 wherein:
   said processor and said memory are provided as part of a frame grabber module; and
   said means for transferring is provided as a direct memory access (DMA) channel coupled between said compensating circuit and said frame grabber module.

6. The system of claim 4 further wherein said processor is coupled to said illumination system to control said illumination system.

7. The system of claim 1 wherein said offset correction circuit comprises an adder circuit having a first port coupled to the first port of said image acquisition circuit and a second port, and wherein said scale correction circuit comprises a multiplier circuit having a first port coupled to the second port of said adder circuit and having a second port corresponding to the output port of said compensating circuit.

8. The system of claim 1 wherein said compensation memory comprises:
   one or more offset memories, each of the one or more offset memories coupled to said adder circuit; and
   one or more scale memories, each of the one or more scale memories coupled to said multiplier circuit.

9. The system of claim 8 wherein:
   said system operates in a plurality of lighting modes;
   said compensating memory comprises a plurality of offset memories, each of said plurality of offset memories adapted for use in a particular one of the plurality of lighting modes, and
   a plurality of scale memories, each of said plurality of scale memories adapted for use in a particular one of the lighting modes.

10. The system of claim 9 further comprising a bank switch having at least one terminal coupled to each of said plurality of offset memories and said plurality of scale memories and having at least one terminal coupled to said processor, wherein in response to a signal from said processor, said bank switch couples at least one of said plurality of offset memories to said adder circuit and at least one of said plurality of scale memories to said multiplier circuit.

* * * * *